United States Patent [19]
Sugiyama et al.

[11] Patent Number: 6,110,348
[45] Date of Patent: Aug. 29, 2000

[54] NOX SENSOR AND MANUFACTURING METHOD OF THE SAME

[75] Inventors: Tomio Sugiyama, Nagoya; Naoto Miwa, Tsushima; Masahiro Shibata, deceased, late of Nagoya, by Midori Shibata, Natsumi Shibata, Raina Shibata, legal representatives; Hiromi Sano, Nagoya, all of Japan

[73] Assignee: Denso Corporation, Kariya, Japan

[21] Appl. No.: 09/092,647

[22] Filed: Jun. 9, 1998

[30] Foreign Application Priority Data

Jun. 11, 1997 [JP] Japan ................................. 9-171015

[51] Int. Cl.$^7$ ................................................. G01N 27/26
[52] U.S. Cl. ........................ 205/425; 204/426; 156/89.11; 156/89.16
[58] Field of Search .................................. 204/425, 426, 204/427; 205/783.5, 784; 156/89.11, 89.12, 89.16

[56] References Cited

U.S. PATENT DOCUMENTS

| | | | |
|---|---|---|---|
| 4,450,065 | 5/1984 | Yamada et al. | 204/425 |
| 4,505,807 | 3/1985 | Yamada | 204/426 |
| 5,281,314 | 1/1994 | Yagi et al. | 204/426 |
| 5,302,275 | 4/1994 | Dietz et al. | 204/424 |
| 5,672,811 | 9/1997 | Kato et al. | |

FOREIGN PATENT DOCUMENTS

8-271476  10/1996  Japan .

*Primary Examiner*—Robert J. Warden, Sr.
*Assistant Examiner*—Kaj K. Olsen
*Attorney, Agent, or Firm*—Pillsbury Madison & Sutro LLP

[57] ABSTRACT

A main body of a NOx sensor has a sensor cell and defines a reference gas chamber and a sample gas chamber therein. The sample gas chamber has a wall formed by a solid electrolytic substrate having an oxygen ion conductivity. The sensor cell is disposed between the reference gas chamber and the sample gas chamber for detecting a concentration of a NOx gas. A pump cell body of the NOx sensor has a surface facing to the sample gas chamber and has a pump cell for introducing and exhausting an oxygen gas to and from the sample gas chamber. In manufacturing this NOx sensor, the main body and the pump cell body are fabricated individually as separate items. The main body and the pump cell body are sintered independently. Then, the main body and the pump cell body are assembled into to the NOx sensor.

5 Claims, 10 Drawing Sheets

NOX SENSOR AND MANUFACTURING METHOD OF THE SAME

BACKGROUND OF THE INVENTION

The present invention relates to a NOx sensor detecting a concentration of NOx in a sample gas, such as an exhaust gas of an internal combustion engine, and relates to a manufacturing method of the NOx sensor.

A conventional NOx sensor, used for detecting the concentration of NOx in a sample gas, utilizes an oxygen ion conductivity of a solid electrolytic substrate (more specifically, an oxygen ion conductivity of a stabilized zirconia etc.) as disclosed in SAE 960334.

Figure 11:
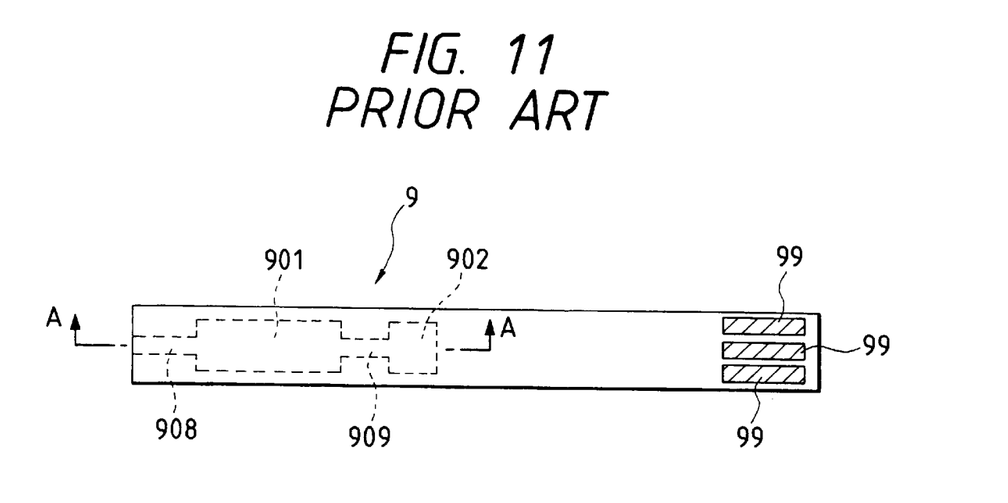
FIG. 11 is a plan view showing a conventional NOx sensor.
Figure 12:
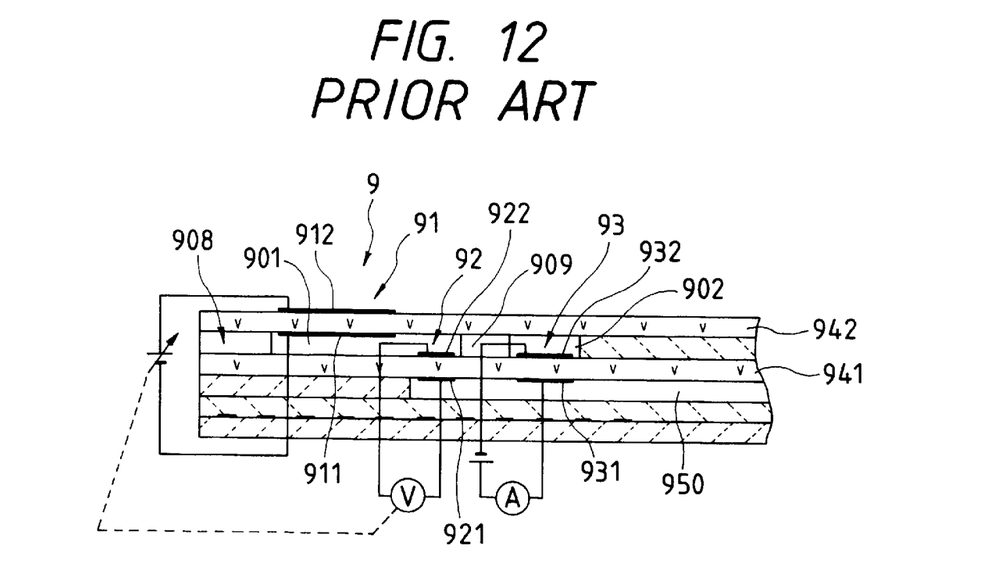
FIG. 12 is a cross-sectional view showing the conventional NOx sensor disclosed in FIG. 11.

FIGS. 11 and 12 show a conventional NOx sensor 9 which comprises a reference gas chamber 950 and a sample gas chamber 902. The sample gas chamber 902 has a bottom and a ceiling defined by a pair of solid electrolytic substrates 941 and 942 each having an oxygen ion conductivity. A sensor cell 93 is provided between the reference gas chamber 950 and the sample gas chamber 902 for detecting the concentration of NOx. The sensor cell 93 has a pair of sensing electrodes 931 and 932 attached on opposite surfaces of the solid electrolytic substrate 941 located between the reference gas chamber 950 and the sample gas chamber 902. The sample gas chamber 902 communicates with another sample gas chamber 901 via a gas passage 909. A sample gas introducing passage 908 is provided adjacent to the sample gas chamber 901.

An oxygen pump cell 91 and an oxygen sensor cell 92 are provided in the sample gas chamber 901. The oxygen pump cell 91 has a pair of oxygen pumping electrodes 911 and 912 attached on opposite surfaces of the solid electrolytic substrate 942 defining the ceiling of the sample gas chamber 901. The oxygen sensor cell 92 has a pair of oxygen sensing electrodes 921 and 922 attached on opposite surfaces of the solid electrolytic substrate 941 defining the bottom of the sample gas chamber 901. The oxygen sensor cell 92 is located between the reference gas chamber 950 and the sample gas chamber 902. One oxygen sensing electrode 921 faces to the reference gas chamber 950. The other oxygen sensing electrode 922 faces to the sample gas chamber 901. The oxygen pump cell 91 and the oxygen sensor cell 92 cooperatively adjust the sample gas to have a constant oxygen concentration.

This conventional NOx sensor detects the NOx concentration in the following manner.

First, a sample gas is introduced into the sample gas chamber 901. The oxygen sensor cell 92 and the oxygen pump cell 91 cooperatively operate to adjust the oxygen gas concentration to a predetermined constant value. The sample gas having a thus adjusted oxygen gas concentration is introduced into the sample gas chamber 902 via the gas passage 909.

The sensing electrode 932 of the sensor cell 93 is an active electrode that ionizes oxygen atoms involved in a NOx gas through a deoxidizing reaction. The ionized oxygen flows across the solid electrolytic substrate 941, causing an ion current having a value proportional to an amount of the NOx gas. Thus, the concentration of the NOx gas can be detected by measuring the ion current.

On the other hand, the electrodes 911 and 922 facing to the sample gas chamber 901 are inactive electrodes having no capability of ionizing the oxygen atoms. The sensing electrode 932 (i.e., active electrode) is made of platinum (Pt). The electrodes 911 and 922 (i.e., inactive electrodes) are made of platinum (Pt) with gold (Au) additives.

Reference numeral 99 in FIG. 11 denotes terminals formed on the edge of the NOx sensor 9.

The NOx sensor 9 is manufactured in the following manner. A plurality of green sheets of a solid electrolytic substrate are prepared. Each electrode is printed on a predetermined position of a corresponding solid electrolytic substrate sheet by using an electrically conductive paste. Then, the solid electrolytic substrate sheets are stacked to form a multilayered sensor body. Finally, the multilayered sensor body is sintered at a time to finally obtain the NOx sensor 9.

However, the above-described conventional NOx sensor 9 has the following problems.

A melting point of Au, i.e., 1,064° C., is so low that Au vaporizes from the electrode in a high-temperature environment when the NOx sensor is sintered according to the above-described conventional manufacturing method. The vaporized Au contaminates the active electrode. The activity of the active electrode is deteriorated by the vaporized Au. This causes a problem in the detection of the NOx concentration.

Many of NOx sensors use an oxygen ion conductive substance of a zirconia group as the solid electrolytic substrate. The sintering temperature of this substance is in a range of 1,400~1,600° C. It means that the above-described contamination problem of the active electrode by the vaporized Au is inevitable for many of the NOx sensors.

SUMMARY OF THE INVENTION

An object of the present invention is to provide a manufacturing method of a NOx sensor capable of preventing the electrode of a sensor cell from being contaminated by the vaporized Au during a sintering process. Furthermore, another object of the present invention is to provide a NOx sensor capable of accurately detecting the concentration of NOx.

In order to accomplish this and other related objects, a first aspect of the present invention provides a manufacturing method for manufacturing a NOx sensor comprising a main body and a pump cell body. The main body has a sensor cell and defines a reference gas chamber and a sample gas chamber therein. The sample gas chamber has a wall formed by a solid electrolytic substrate having an oxygen ion conductivity. The sensor cell is disposed between the reference gas chamber and the sample gas chamber for detecting a concentration of a NOx gas. The pump cell body has a surface facing to the sample gas chamber and has a pump cell for introducing and exhausting an oxygen gas to and from the sample gas chamber. The manufacturing method according to the present invention comprises the steps of fabricating the main body and the pump cell body as separate items, sintering the main body and the pump cell body independently, and assembling the main body and the pump cell body after finishing the sintering operation to obtain a NOx sensor.

Preferably, the pump cell body is coupled with a coupling groove formed on the main body and then the pump cell body is bonded with the main body by an adhesive.

More specifically, the main body and the pump cell body are sintered independently at a temperature exceeding a melting point of a substance vaporizable from the pump cell. The substance vaporizable from the pump cell is an additive, such as Au, added to the main material, such as, Pt, Rh and Pt/Rh, of an electrode of the pump cell. This additive suppresses an activity of the electrode of the pump cell.

Preferably, a united assembly of the main body and the pump cell body is thermally processed at a temperature lower than the melting point of the substance vaporizable from the pumping cell.

A second aspect of the present invention provides a sensor capable of accurately detecting a concentration of NOx in a sample gas. The sensor comprises a main body having a sensor cell and defining a reference gas chamber and a sample gas chamber therein. The sample gas chamber has a wall formed by a solid electrolytic substrate having an oxygen ion conductivity. The sensor cell is disposed between the reference gas chamber and the sample gas chamber for detecting a concentration of a NOx gas. A pump cell body has a surface facing to the sample gas chamber and has a pump cell for introducing and exhausting an oxygen gas to and from the sample gas chamber. No electrode of the sensor cell is contaminated by a substance evaporating from the pump cell during a sintering operation by independently sintering the main body and the pump cell body.

Preferably, the main body has a coupling groove with which the pump cell body is coupled, and the pump cell body is bonded with the main body by an adhesive.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Preferred embodiments of the present invention will be explained hereinafter with reference to attached drawings. Identical parts are denoted by the same reference numerals throughout the views.

First Embodiment

FIGS. 1 through 5 are views showing a manufacturing method of a NOx sensor and a detailed arrangement of this NOx sensor in accordance with the first embodiment of the present invention.

Figure 1:
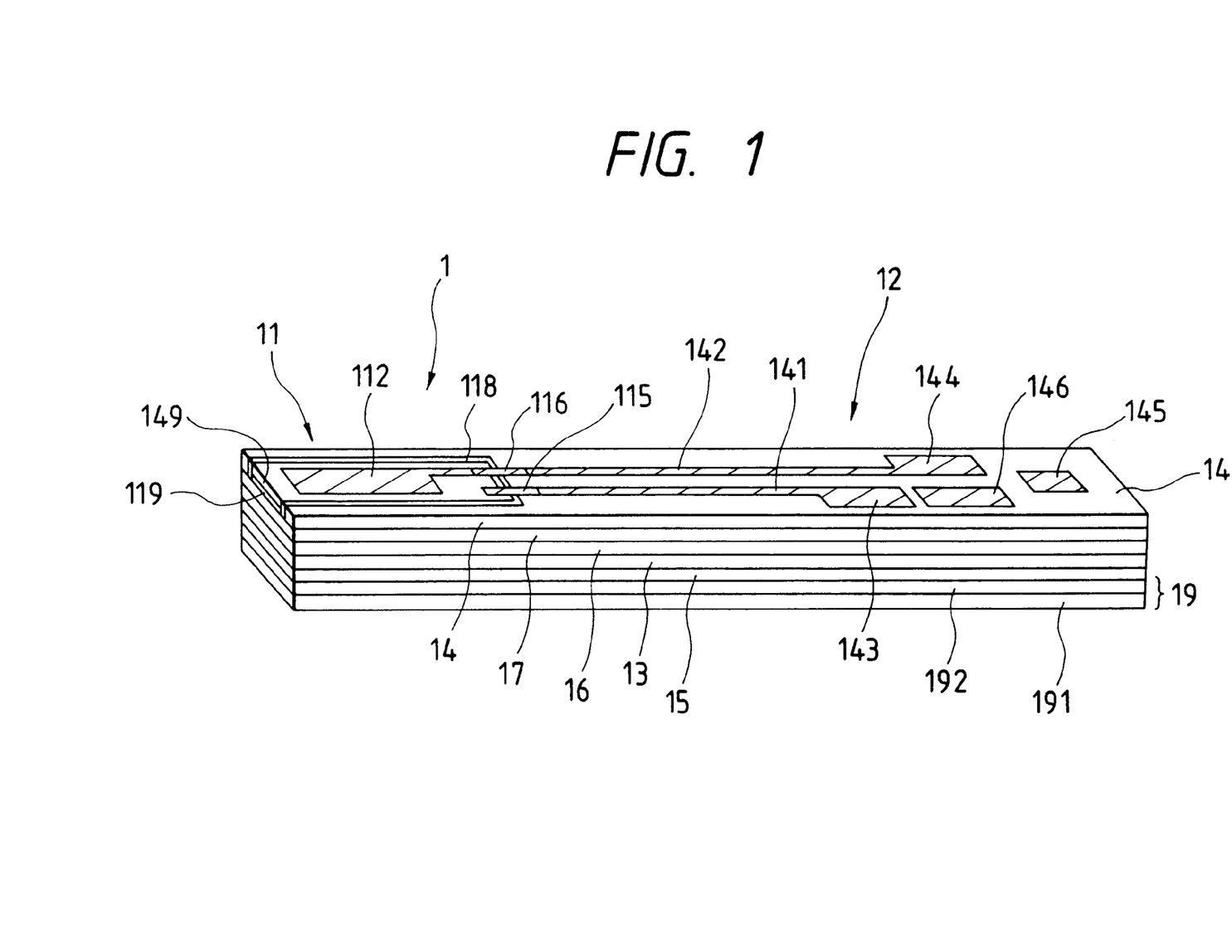
FIG. 1 is a perspective view showing an overall arrangement of a NOx sensor in accordance with a first embodiment of the present invention.
Figure 2:
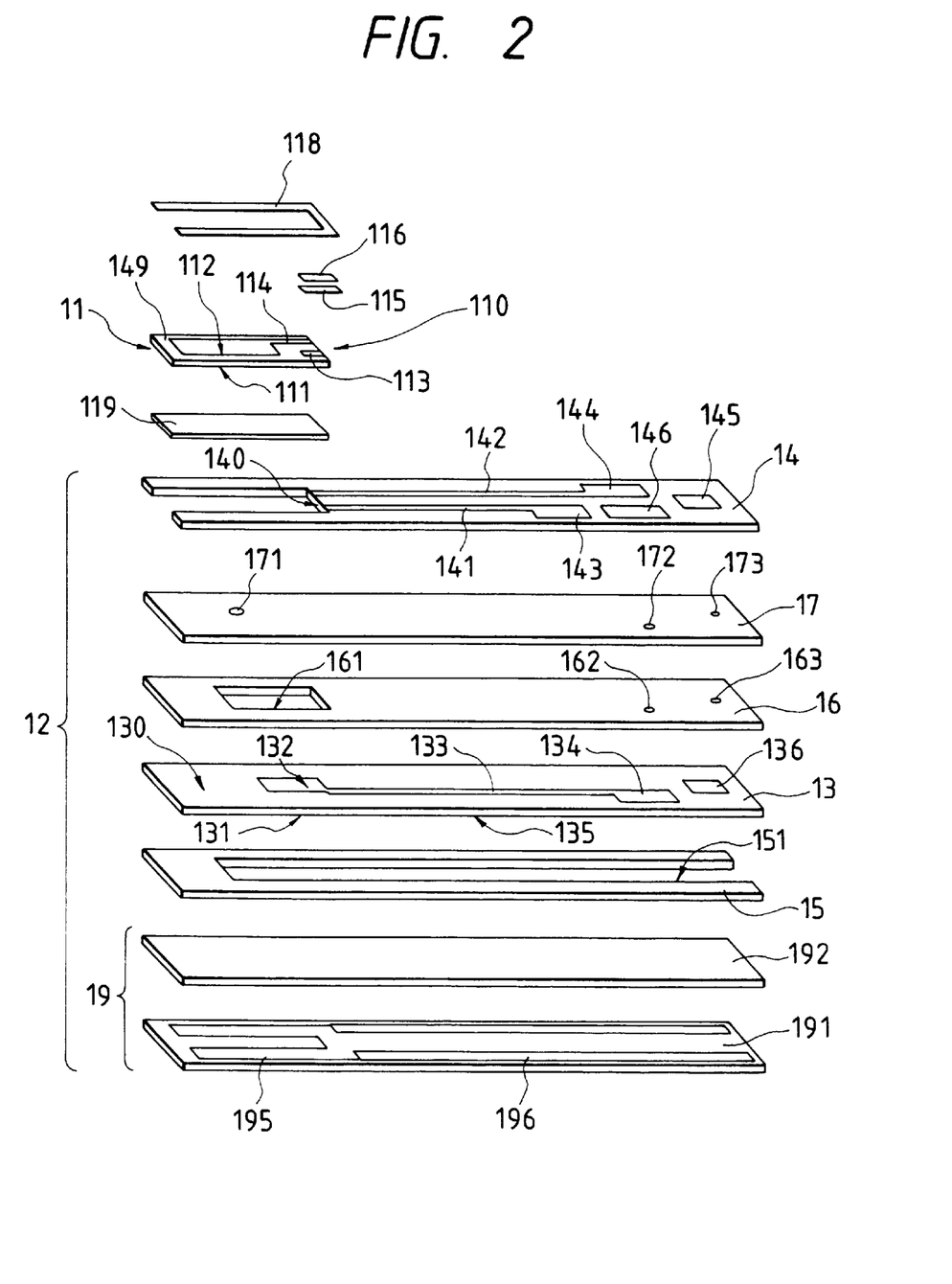
FIG. 2 is an exploded perspective view showing the NOx sensor in accordance with a first embodiment of the present invention.

As shown in FIGS. 1 and 2, a NOx sensor 1 of this embodiment comprises a main body 12 comprising a reference gas chamber 151 and a sample gas chamber 161. The sample gas chamber 161 has a bottom defined by a solid electrolytic substrate 13 having an oxygen ion conductivity. A sensor cell 130, detecting the concentration of NOx, is provided between the reference gas chamber 151 and the sample gas chamber 161. Furthermore, the NOx sensor 1 comprises a pump cell body 11 with a pump cell 110 for introducing and exhausting an oxygen gas to and from the sample gas chamber 161.

The sensor cell 130 includes a sensing electrode 132 facing to the sample gas chamber 161 defined in the solid electrolytic substrate 13 and another sensing electrode 131 facing to the reference gas chamber 151.

The pump cell 110 is provided on a solid electrolytic substrate 149. A pumping electrode 111, facing to a sample gas diffusive resistor layer 119, is provided on a lower surface of the solid electrolytic substrate 149. Another pumping electrode 112, exposing to the outside space of the NOx sensor 1, is provided on an opposite (i.e., an upper) surface of the solid electrolytic substrate 149.

The pumping electrode 111 is an inactive electrode having no NOx activation function. On the other hand, the pumping electrode 112 and sensing electrodes 131 and 132 are active electrodes having the capability of ionizing the oxygen atoms (i.e., having a NOx activation function). It may be possible to replace the electrodes 112 and 131 with the inactive electrodes.

When the above-described NOx sensor 1 is manufactured, the main body 12 and the pump cell body 11 are fabricated as separated items (i.e., partly-fabricated items). The separate main body 12 and pump cell body 11 are sintered independently. Thereafter, the main body 12 and pump cell body 11 are assembled or united to obtain the NOx sensor 1.

Next, details of the NOx sensor will be explained.

As shown in FIGS. 1 and 2, the main body 12 comprises a heater element 195 and leads 196 interposed between first and second insulating substrates 191 and 192. The heater element 195, leads 196 and insulating substrates 191 and 192 constitute a heater 19. A third insulating substrate 15, mounted on the second insulating substrate 192, has an elongated slit that defines the reference gas chamber 151. The solid electrolytic substrate 13, having the sensor cell 130, is mounted on the third insulating substrate 15. A fourth insulating substrate 16, mounted on the solid electrolytic substrate 13, has a window that defines the sample gas chamber 161. A fifth insulating substrate 17, mounted on the fourth insulating substrate 16, has a pin hole 171. A sixth insulating substrate 14, mounted on the fifth insulating substrate 17, has a coupling groove 140 with which the pump cell body 11 is coupled.

The sensing electrodes 131 and 132 of sensor cell 130 are formed on opposite surfaces of the solid electrolytic substrate 13 in a back-to-back relationship. The sensing electrodes 131 and 132 are connected to intermediate terminals 134 and 136 via leads 133 and 135 formed on the upper and lower surfaces of the solid electrolytic substrate 13, respectively. Although FIG. 2 is not clear, the sensing electrode 131 and the lead 135 are provided on the lower surface of the solid electrolytic substrate 13. The lead 135 is connected to the intermediate terminal 136 via a through hole (not shown) extending from the lower surface to the upper surface of the solid electrolytic substrate 13.

The fourth insulating substrate 16 has through holes 162 and 163. The fifth insulating substrate 17 has through holes 172 and 173. The intermediate terminal 134 formed on the solid electrolytic substrate 13 is connected with a terminal 146 formed on the sixth insulating substrate 14 via the through holes 162 and 172 in which an electrically conductive substance is filled. Similarly, the intermediate terminal 136 formed on the solid electrolytic substrate 13 is connected with a terminal 145 formed on the sixth insulating substrate 14 via the through holes 163 and 173 in which an electrically conductive substance is filled.

Furthermore, the pin hole 171 serves as a sample gas introducing passage introducing a sample gas into the sample gas chamber 161.

The sixth insulating substrate 14 has terminals 143~146 and leads 141~142. The terminals 145 and 146 serve as signal output terminals of the sensor cell 130. The terminals 143 and 144 are connected to pumping electrodes 111 and 112 via leads 141 and 142, respectively.

The pumping electrodes 111 and 112 of the pump cell 110 are formed on opposite surfaces of the solid electrolytic substrate 149 in a back-to-back relationship. Outlet terminals 113 and 114 are formed at an edge of the solid electrolytic substrate 149 to connect the pumping electrodes 111 and 112 to the leads 141 and 142 formed on the sixth insulating substrate 14, respectively. Electrical conductors 115 and 116 are provided to ensure the electric connection between the outlet terminals 113, 114 and the leads 141 and 142. The sample gas diffusive resistor layer 119 is provided underneath the solid electrolytic substrate 149. The pump cell body 11, inserted in the coupling groove 140, is bonded with the sixth insulating substrate 14 by an adhesive layer 118.

A manufacturing method of the above-described NOx sensor 1 will be explained hereinafter.

First, a manufacturing method of a zirconic green sheet is explained. The zirconic green sheet is used to form the solid electrolytic substrates 13 and 149. A main material of the zirconia green sheet is a yttria partially-stabilized zirconia with an average particle diameter of 0.5 $\mu$m. This yttria partially-stabilized zirconia comprises 6 mol % yttria and 94 mol % zirconia. The weighing capacity of the yttria partially-stabilized zirconia is 100 weight parts. As subsidiary materials, an $\alpha$-alumina is one weight part, a PVB (polyvinyl butyral) is five weight parts, a DBP (di-butyl phthalate) is 10 weight parts, an ethanol is 10 weight parts, and a toluene is 10 weight parts.

Then, the prepared yttria partially-stabilized zirconia, $\alpha$-alumina, PVB, DBP, ethanol and toluene are mixed in a ball mill to obtain a slurry of them. The obtained slurry is configured into a sheet body using a doctor blade method. The fabricated sheet body is 0.3 mm thick in a dried condition. A rectangular piece of 5 mm×70 mm is cut out of this sheet for the solid electrolytic substrate 13. Similarly, a rectangular piece of 4 mm×25 mm is cut out of this sheet for the solid electrolytic substrate 149.

Next, to form the pumping electrode 111, an electrically conductive paste is printed on the fabricated sheet body of the solid electrolytic substrate 149. This conductive paste is a Pt paste with an additive of 1~10 wt % Au. The other electrode 112 and outlet terminals 113 and 114 are formed by printing a Pt paste with an additive of 10 wt % zirconia.

Next, a through hole is opened across the fabricated sheet body of the solid electrolytic substrate 13. The through hole extends in a width direction of the fabricated sheet body of the solid electrolytic substrate 13. Then, to form the sensing electrodes 131 and 132, leads 133 and 135 and intermediate terminals 134 and 136, a Pt paste with additives of 0~10 wt % Pd and 10 wt % zirconia is printed on the fabricated sheet body of the solid electrolytic substrate 13.

Next, a manufacturing method of an alumina green sheet is explained. The alumina green sheet is used to form the first to sixth insulating substrates 191, 192, 15, 16, 17 and 14. A main material of the aluminum green sheet is an $\alpha$-alumina with an average particle diameter of 0.3 $\mu$m. The weighing capacity of this $\alpha$-alumina is 98 weight parts. As subsidiary materials, a yttria partially-stabilized zirconia, comprising 6 mol % yttria and 94 mol % zirconia, is three weight parts. Furthermore, a PVB (polyvinyl butyral) is 10 weight parts, a DBP (di-butyl phthalate) is 10 weight parts, an ethanol is 30 weight parts, and a toluene is 30 weight parts.

Then, the prepared $\alpha$-alumina, yttria partially-stabilized zirconia, PVB, DBP, ethanol and toluene are mixed in a ball mill to obtain a slurry of them. The obtained slurry is configured into a sheet body using a doctor blade method. The fabricated sheet body is 0.3 mm thick in a dried condition. A rectangular piece of 5 mm×70 mm is cut out of this sheet body for each of the first to sixth insulating substrates 191, 192, 15~17 and 14.

Next, to form the leads 141 and 142 and the terminals 143~146, a Pt paste with an additive of 10 wt % zirconia is printed on the fabricated sheet body of the sixth insulating substrate 14. Then, one end portion of the fabricated sheet body of the sixth insulating substrate 14 is cut into a U-shaped configuration to leave a slit serving as the coupling groove 140 with which the pump cell body 11 is coupled.

The through holes 172 and 173 and the pin hole 171 are opened across a fabricated sheet body of the fifth insulating substrate 17. Each of through holes 172 and 173 extends in a width direction of the fabricated sheet body of the fifth insulating substrate 17. The through holes 162 and 163 and a window serving as the sample gas chamber 161 are opened across a fabricated sheet body of the fourth insulating substrate 16. Each of through holes 162 and 163 extends in a width direction of the fabricated sheet body of the fourth insulating substrate 16. The fabricated sheet body of the third insulating substrate 15 is cut into an elongated U-shaped configuration to leave an elongated slit serving as the reference gas chamber 151. Furthermore, to form the heater element 195 and the leads 196, an electrically conductive paste with additives of 90 wt % Pt and 10 wt % alumina is printed on the fabricated sheet body of the first insulating substrate 191.

Each through hole is filled with a Pt paste with an additive of 10 wt % zirconia.

Then, to form a multilayered assembly, the fabricated sheet bodies of solid electrolytic substrate 13 and insulating substrates 14~17, 191 and 192 are stacked and bonded under a pressure by using a pressure-sensitive adhesive paste having an adhesive property at a room temperature.

Next, to obtain the pump cell body 11, the fabricated sheet body of the pump cell body 11 is sintered at 1,500° C. for one hour. Furthermore, to obtain the main body 12, the multilayered assembly is sintered in an atmospheric environment at 1,500° C. for one hour.

Next, an adhesive alumina paste is applied in the coupling groove 140 of the main body 12. Then, the pump cell body 11 is coupled with the coupling groove 140.

Next, the Pt paste is applied on the coupled pump cell 11 and main body 12 to ensure the electric connection between the terminals 113 and 114 and the leads 141 and 142, respectively. Thereafter, the Pt paste is thermally processed at 950° C.

Furthermore, the pump cell body 11, inserted in the coupling groove 140, is securely fixed with the sixth insulating substrate 14 by providing the adhesive layer 118. The adhesive layer 118 is preferably made of a high melting-point glass paste with an additive of alumina of five weight parts. Then, the united assembly of the pump cell 11 and main body 12 is thermally processed in an atomospheric environment at 950° C. for one hour. Thus, the NOx sensor 1 is finally obtained.

Next, the performance of the NOx sensor 1 in accordance with this embodiment will be explained in comparison with a NOx sensor 8 manufactured according to a conventional method.

Figure 3:
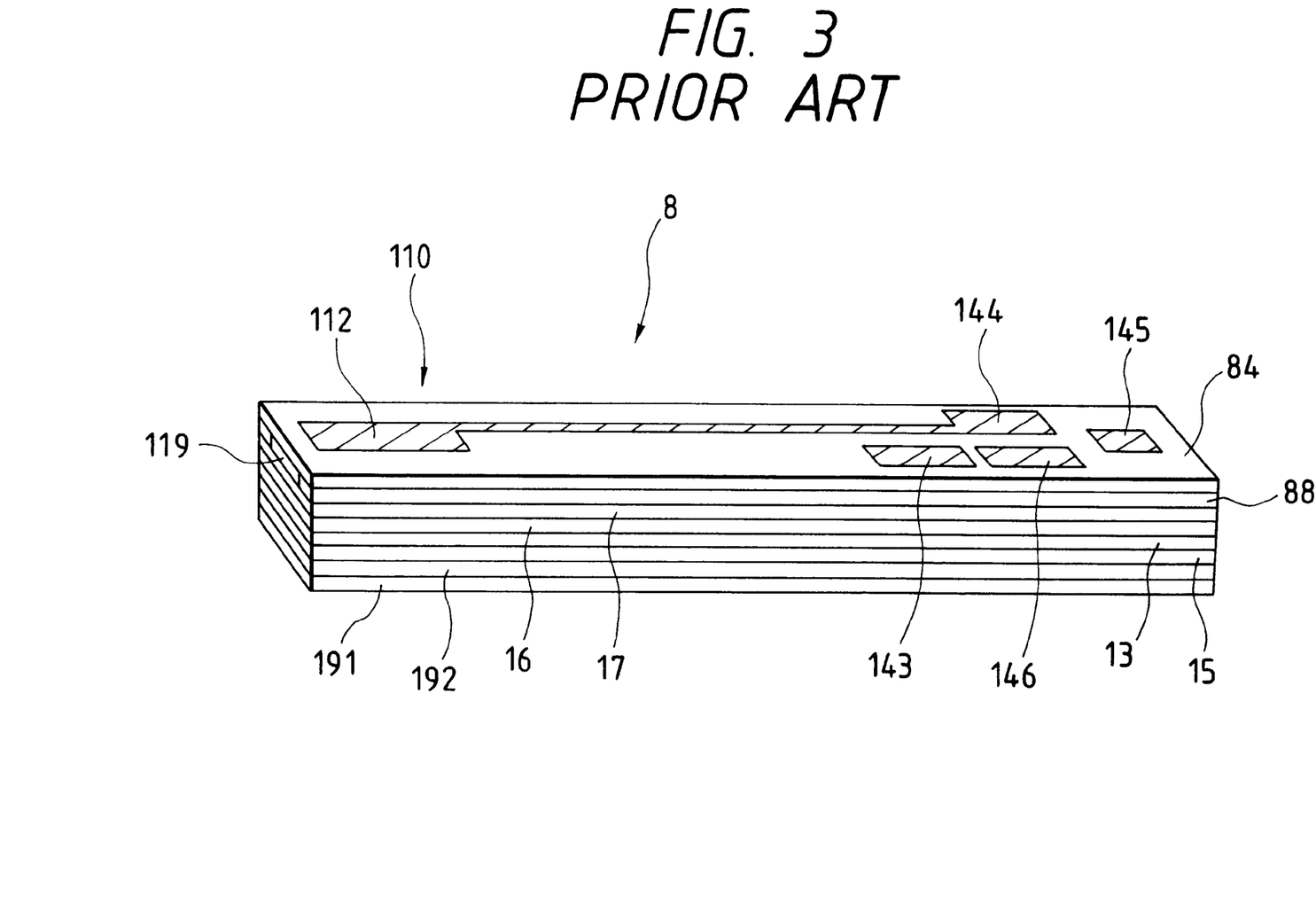
FIG. 3 is a perspective view showing an overall arrangement of a comparative conventional NOx sensor.
Figure 4:
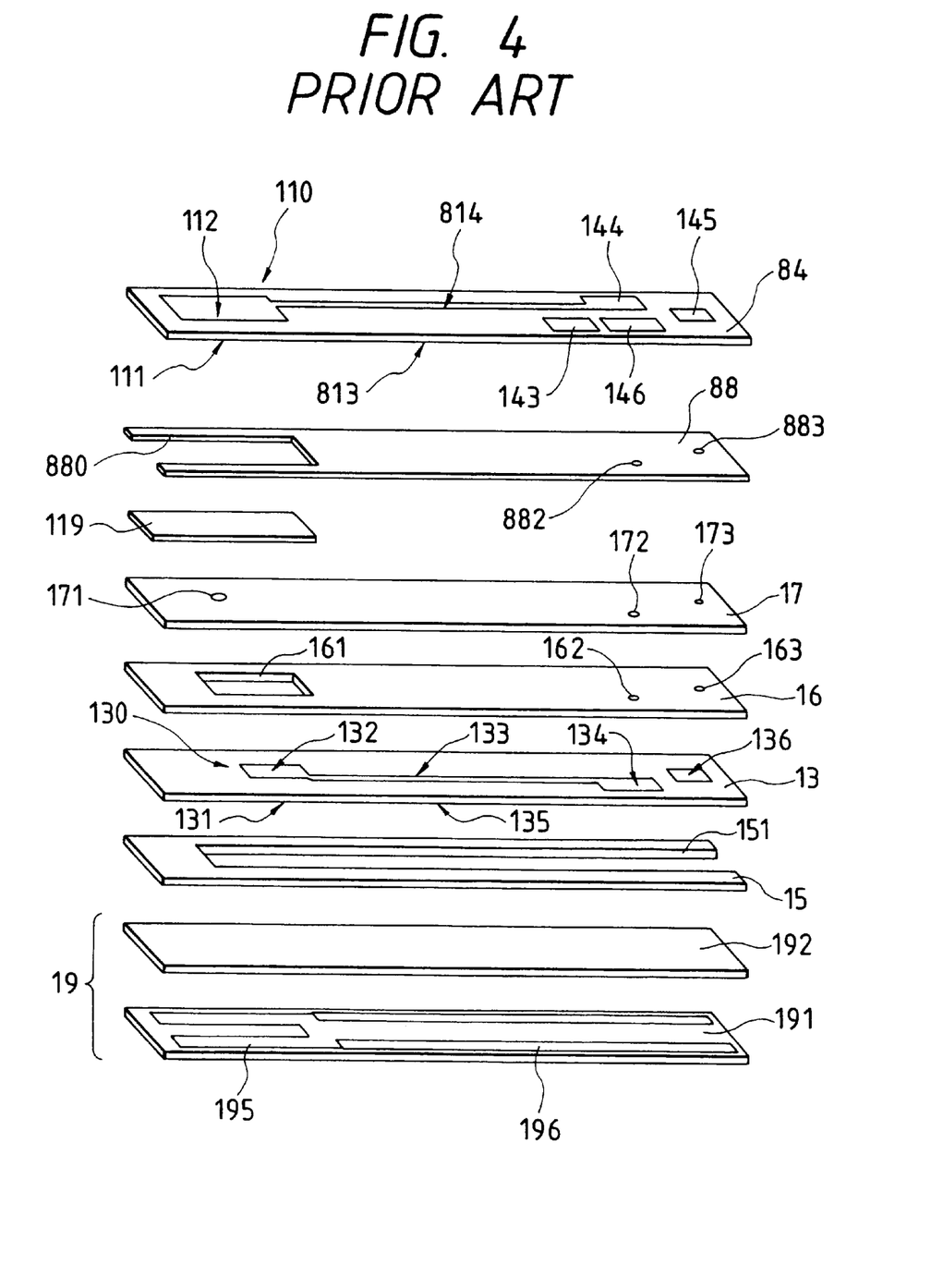
FIG. 4 is an exploded perspective view showing the comparative conventional NOx sensor disclosed in FIG. 3.

FIGS. 3 and 4 show a detailed arrangement of the conventional NOx sensor 8 used in a comparative performance test.

As shown in FIGS. 3 and 4, the NOx sensor 8 comprises a solid electrolytic substrate 84 having a pump cell 110. An insulating substrate 88 is positioned beneath the solid electrolytic substrate 84. The insulating substrate 88 has a U-shaped cutout 880 in which a sample gas diffusive resistor layer 119 is positioned. Through holes 882 and 883 are opened across the insulating substrate 88. Each of the through holes 882 and 883 extends in a width direction of the insulating substrate 88 for electrically connecting intermediate terminals 134 and 136 to output terminals 146 and 145, respectively. The rest of the arrangement is substantially the same as the above-described NOx sensor 1 shown in FIGS. 1 and 2.

The conventional NOx sensor 8 is manufactured in the following manner. A plurality of sheet bodies are fabricated for the solid electrolytic substrates 13 and 84 and the insulating substrates 15~17 and 88. A print paste is applied on some of fabricated sheet bodies to form the required electrode and lead. Some of the fabricated sheet bodies are configured in a predetermined shape as shown in FIG. 4. Then, the sheet bodies are stacked and bonded into a multilayered assembly. Then, the multilayered assembly is sintered at 1,500° C. to obtain the NOx sensor 8. According to this conventional manufacturing method, the pumping electrodes 111 and 112 of the pump cell 110 and the sensing electrodes 131 and 132 of the sensor cell 130 are simultaneously sintered.

The comparative performance test for comparing the NOx sensor 1 and the NOx sensor 8 was performed in the following manner. A gas temperature was set to 400° C. The used sample gas included NO, whose concentration was varied in a range of 0~5,000 ppm, and 5% $O_2/N_2$ (1.2 liter/min). The temperature of the NOx sensor 1 and the NOx sensor 8 was maintained at 750° C.

Figure 5:
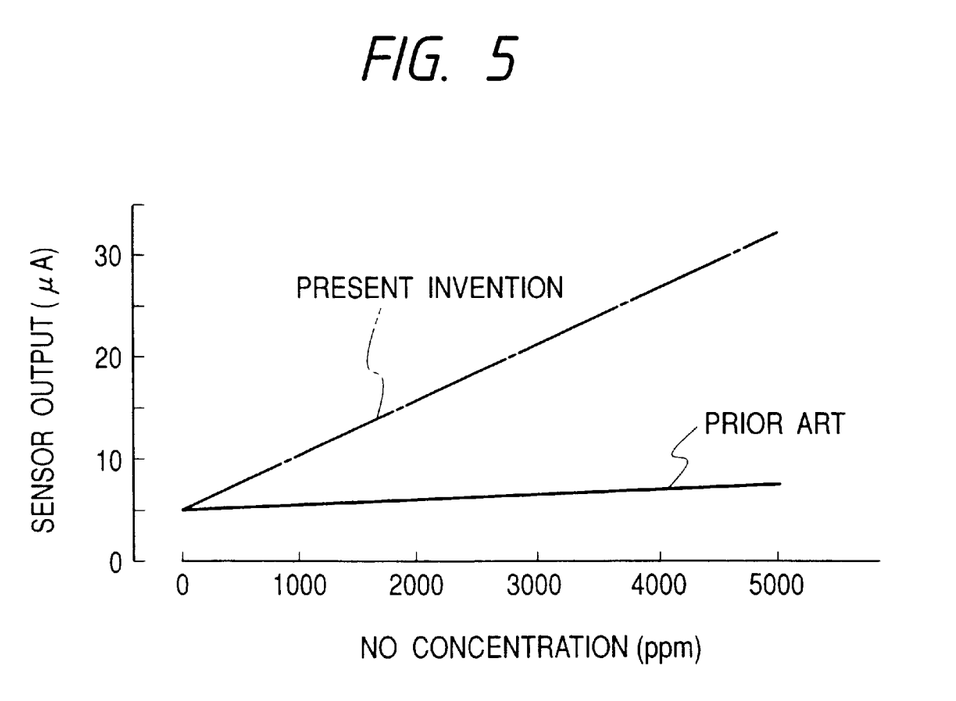
FIG. 5 is a graph showing a relationship between a sensor output and a NO concentration in accordance with the first embodiment of the present invention in comparison with a relationship in the conventional sensor.

FIG. 5 is a graph showing a relationship between the NO concentration and a corresponding sensor output obtained as a result of the comparative performance test. As apparent from the graph of FIG. 5, the NOx sensor 1 of this embodiment can produce a sensor output varying with a larger gradient with respect to the NOx concentration, compared with the conventional NOx sensor 8.

An EPMA analysis was conducted to investigate the reason why the conventional NOx sensor 8 produced a sensor output varying with a smaller gradient. According to this EPMA analysis, a small amount of Au was found on the surface of the sensing electrode 132 of the sensor cell 130 of the conventional NOx sensor 8. In other words, the sensing electrode 132 was contaminated by Au. This is a drawback of the conventional manufacturing method according to which the pumping electrodes 111 and 112 of the pump cell 110 and the sensing electrodes 131 and 132 of the sensor cell 130 are simultaneously sintered.

When the pumping electrodes 111 and 112 and the sensing electrodes 131 and 132 are simultaneously sintered, Au evaporates from the pumping electrode 111 and diffuses through the sample gas diffusive resistor layer 119, the pin hole 171 and the sample gas chamber 161 to the sensing electrode 132 of the sensor cell 130. Thus, the evaporated and diffused Au deteriorates the activity of the sensing electrode 132.

Furthermore, it was found that the sensor output of the conventional NOx sensor 8 was influenced by the degree of the contamination of Au at the sensing electrode 132, causing a significant dispersion in the sensor output value.

As apparent from the foregoing description, the manufacturing method of the present invention differs from the conventional manufacturing method in that the pump cell body 11 having the pump cell 110 is fabricated as a separate item independent of the main body 12 having the sensor cell 130. The pump cell 110 is sintered separately from the sensor cell 130. After finishing the sintering operation of each of the pump cell body 11 and the main body 12, the pump cell body 11 and the main body 12 are united to obtain the NOx sensor 1.

According to the present invention, the pump cell 110 can be separated from the sensor cell 130 during the sintering operation. This effectively prevents the sensing electrode 132 from being contaminated by the Au vaporized and diffused from the pumping electrode 111.

The present invention is not limited to the NOx sensor 1 shown in FIGS. 1 and 2. The present invention can be realized by amending the manufacturing method of the NOx sensor 8 shown in FIGS. 3 and 4. For example, to bring the effects of the present invention, the solid electrolytic substrate 84 having the pump cell 110 and the remainder of the NOx sensor 8 can be separately sintered before they are assembled.

Second Embodiment

Figure 6:
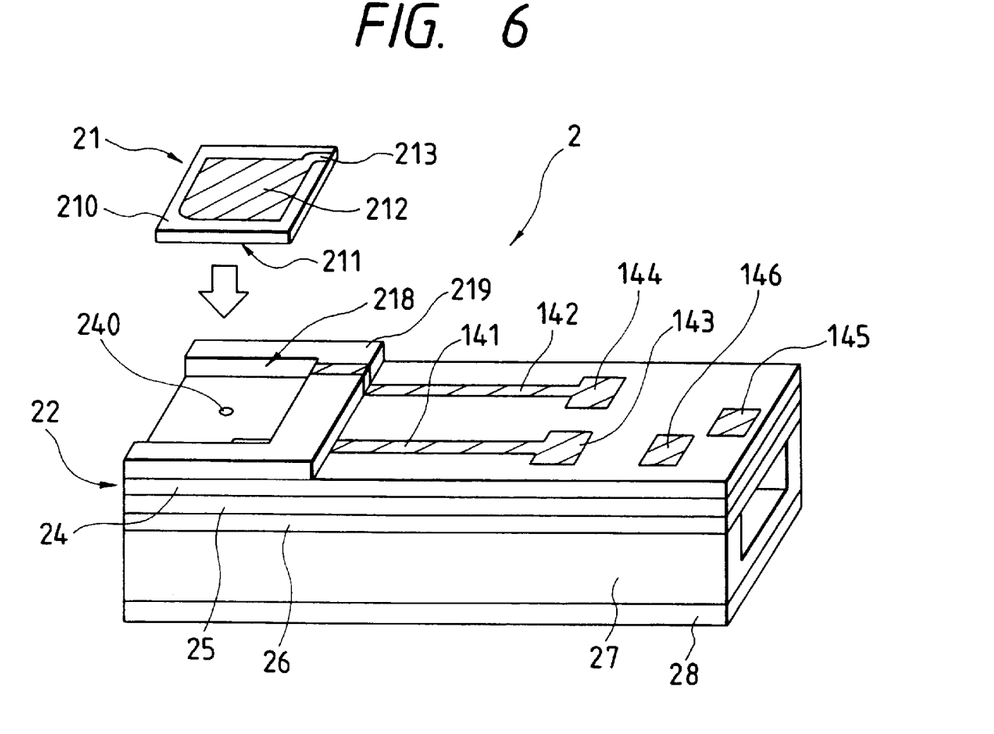
FIG. 6 is a perspective view showing an arrangement of a NOx sensor in accordance with a second embodiment of the present invention.
Figure 7:
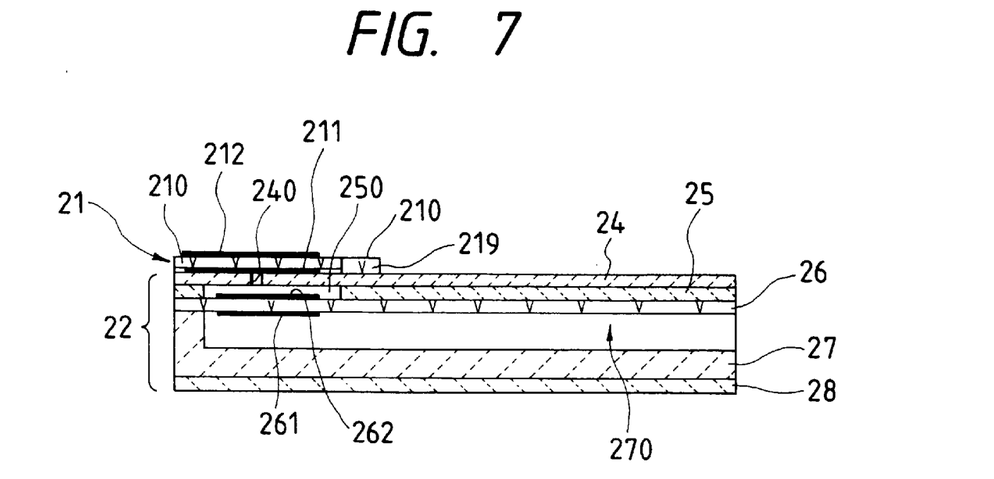
FIG. 7 is a cross-sectional view showing the NOx sensor in accordance with the second embodiment of the present invention.

FIGS. 6 and 7 show a NOx sensor 2 in accordance with a second embodiment of the present invention.

The NOx sensor 2 comprises a main body 22 as a multilayered assembly of insulating substrates 219, 24, 25, 27 and 28 and a solid electrolytic substrate 26.

The insulating substrate 28 is a heater substrate having a heater element serving as a heater of the NOx sensor 2. The insulating substrate 27 has a groove serving as a reference gas chamber 270.

The solid electrolytic substrate 26 has a sensor cell comprising a pair of sensing electrodes 261 and 262 provided on opposite surfaces of the solid electrolytic substrate 26 in a back-to-back relationship. One sensing electrode 261 faces to the reference gas chamber 270. The other sensing electrode 263 faces to a sample gas chamber 250.

The insulating substrate 25 has a window defining the sample gas chamber 250. The insulating substrate 24 has a pin hole 240 serving as a diffusive resistor hole for the sample gas.

A pump cell body 21 comprises a solid electrolytic substrate having opposite surfaces on which pumping electrodes 211 and 212 of a pump cell 210 are provided.

The insulating substrate 24 has lead 141 and 142 and terminals 143 and 144 formed on the surface thereof. The pumping electrodes 211 and 212 of the pump cell body 21 are electrically connected to the terminals 143 and 144 via the leads 141 and 142, respectively. The insulating substrate 219 is formed into a U-shaped configuration to form a recess 218. The lead 141 extends along an upper surface of the insulating substrate 24 and is brought into contact with the lower pumping electrode 211 of the pump cell 210. Another lead 142 extends along the upper surface of the insulating substrate 24 and steps up along a side surface of the insulating substrate 219, then extending along an upper surface of the insulating substrate 219, and is brought into contact with the upper pumping electrode 212 of the pump cell 210.

Instead of extending the lead 142 along the side and upper surfaces of the insulating substrate 219, it is possible to independently form a lead portion on the insulating substrate 219 and on the insulating substrate 24 beforehand. In this case, the separately formed leads are connected when the insulating substrate 219 and the insulating substrate 24 are assembled to form an extended lead portion in substantially the same manner as shown in FIG. 6.

The U-shaped portion of the insulating substrate 219 and the upper surface of the insulating substrate 24 cooperatively define a coupling groove with which the pump cell body 21 is coupled.

Next, a manufacturing method of the NOx sensor 2 will be explained.

A sheet body of the pump cell body 21 is fabricated by using the same materials and the same processes as those disclosed in the first embodiment. A multilayered assembly of main body 22 is fabricated by using the same materials and the same processes as those disclosed in the first embodiment. However, the insulating substrate 27 is fabricated by injection molding a slurry made from an original material.

The fabricated sheet body of the pump cell body 21 is sintered separately from the fabricated multilayered assembly of the main body 22. After finishing the sintering operation of each of the pump cell body 21 and the main body 22, the pump cell body 21 is coupled into the coupling groove of the main body 22. Next, a clearance between the pump cell body 21 and the coupling groove is filled with an adhesive.

The pumping electrode 211 of the pump cell body 21 is brought into contact with the lead 141 provided on the insulating substrate 24. Another pumping electrode 212 has an extended portion 213 brought into contact with the edge of lead 142 provided on the insulating substrate 219. To ensure an electrical connection, an electrically conductive paste is applied to the connecting portions of the electrodes and corresponding leads.

After the pump cell body 21 and the main body 22 are integrated, both bodies 21 and 22 are sintered at 1,000° C. to finally obtain the NOx sensor 2.

The rest of the second embodiment is substantially the same as the first embodiment. Thus, the second embodiment brings substantially the same functions and effects as the first embodiment.

Third Embodiment

Figure 8:
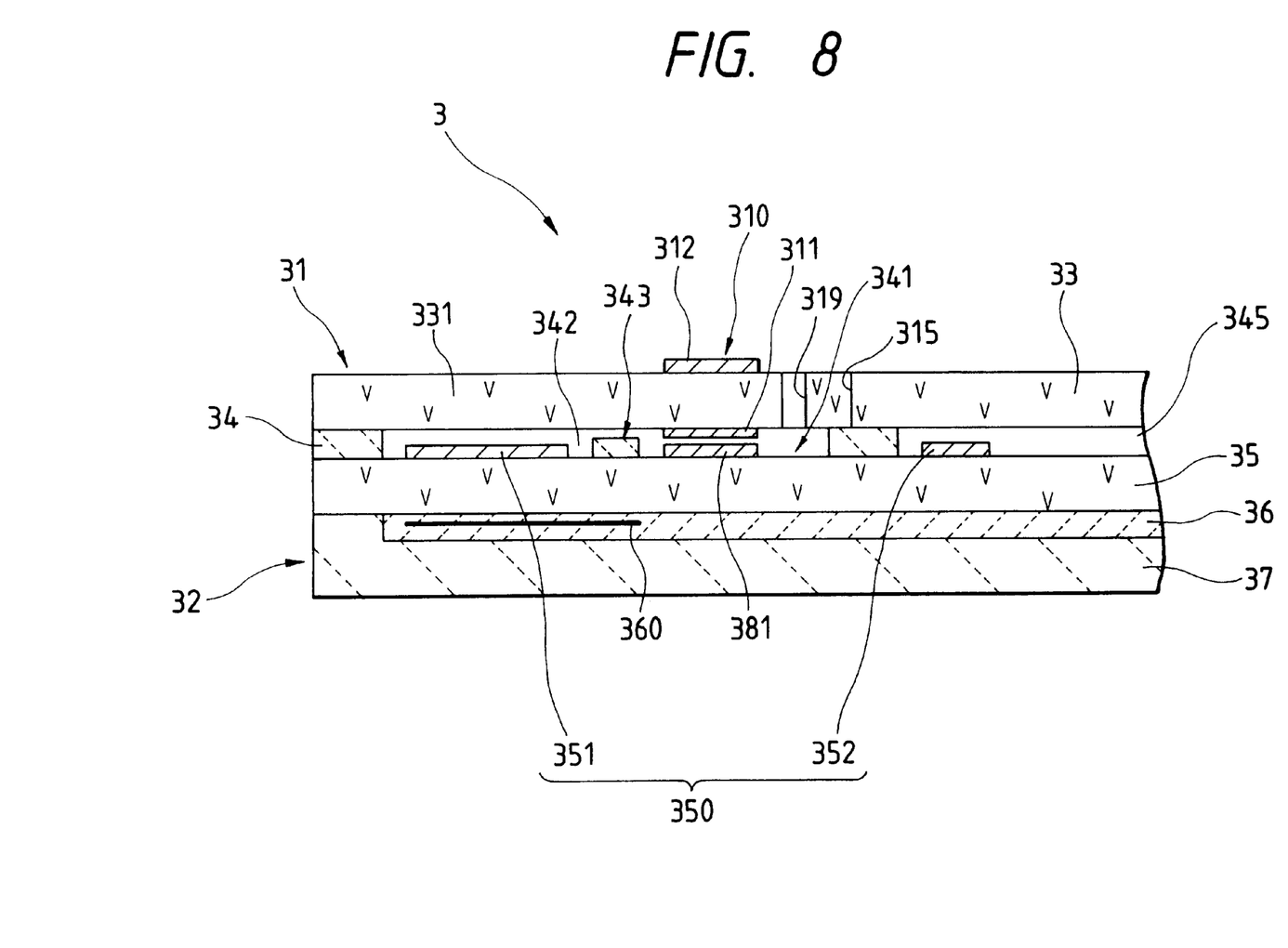
FIG. 8 is a cross-sectional view showing an arrangement of a NOx sensor in accordance with a third embodiment of the present invention.

FIG. 8 shows a NOx sensor 3 in accordance with a third embodiment of the present invention. The NOx sensor 3 has a sample gas chamber and a reference gas chamber provided at a same surface level, as well as an oxygen sensor sell.

As shown in FIG. 8, the NOx sensor 3 comprises a pump cell body 31 and a main body 32. The pump cell body 31 comprises a solid electrolytic substrate 331 and a pump cell 310 having a pair of pumping electrodes 311 and 312. The pumping electrodes 311 and 312 are provided on opposite surfaces of the solid electrolytic substrate 331 in a back-to-back relationship. The pump cell body 31 comprises a pin hole 319 for introducing a sample gas to a first sample gas chamber 341.

The main body 32 has an insulating substrate 37. A heater layer 36 is provided in a recess formed on an upper surface of the insulating substrate 37. The heater layer 36 has a built-in heat generating element 360. A solid electrolytic substrate 35 is disposed on an upper surface of the insulating substrate 37 (i.e., on an upper surface of the heater layer 36). An insulating substrate 34, having two windows, is mounted on the solid electrolytic substrate 35. A solid electrolytic substrate 33 is mounted on the insulating substrate 34. The solid electrolytic substrate 331 of the pump cell body 31 is also mounted on the insulating substrate 34.

One window of the insulating substrate 34 is a common opening for forming the first sample gas chamber 341 and a second sample gas chamber 342 each having a bottom defined by the solid electrolytic substrate 35 and a ceiling defined by the solid electrolytic substrate 331. The other window of the insulating substrate 34 forms a reference gas chamber 345 having a bottom defined by the solid electrolytic substrate 35 and a ceiling defined by the solid electrolytic substrate 33. The first sample gas chamber 341 communicates with the second sample gas chamber 342 via a passage 343.

A sensor cell 350 is provided on the upper surface of the solid electrolytic substrate 35. The sensor cell 350 comprises a sensing electrode 351 facing to the second sampling gas chamber 342 and another sensing electrode 352 facing to the reference gas chamber 345. An oxygen sensing electrode 381, facing to the first sample gas chamber 341, is provided on the upper surface of the solid electrolytic substrate 35. The oxygen sensing electrode 381 and the sensing electrode 352 cooperatively constitute an oxygen sensor cell. The solid electrolytic substrate 33 has an edge 315 serving as a coupling groove with which the pump cell body 31 is coupled. The rest of the arrangement is substantially the same as the first embodiment.

According to the arrangement of the NOx sensor 3, the first and second sample gas chambers 341 and 342 are provided at the same surface level as the reference gas chamber 345. This is advantageous in that the thickness of the NOx sensor 3 can be reduced and the heater layer 36 can be located closely to the electrodes 351 and 352. In other words, this embodiment provides a compact NOx sensor having a quick warm-up ability.

Furthermore, the NOx sensor 3 can function as an oxygen sensor by providing a voltmeter between the oxygen sensing electrode 381 and the sensing electrode 352, as the oxygen sensing electrode 381 faces to the first sample gas chamber 341 while the sensing electrode 352 faces to the reference gas chamber 352. Thus, the voltmeter measures an electromotive force produced between the electrodes 381 and 352 which represents the oxygen concentration of a sample gas.

Furthermore, a feedback circuit is disposed between the oxygen sensor cell and the pump cell 310 to activate the pump cell 310 based on an output value of the oxygen sensor cell. With this arrangement, the oxygen gas concentration in the first sample gas chamber 341 and the second gas chamber 342 can be maintained at a constant value.

Accordingly, the third embodiment provides the NOx sensor 3 capable of accurately detecting the NOx concentration of a sample gas.

Furthermore, as shown in FIG. 8, the electrode 352 is a common electrode acting as one of the electrodes constituting the sensor cell 350 as well as one of the electrodes constituting the oxygen sensor cell. This simplifies the structure of the NOx sensor 3. The third embodiment brings substantially the same functions and effects as the first embodiment.

Fourth Embodiment

Figure 9:
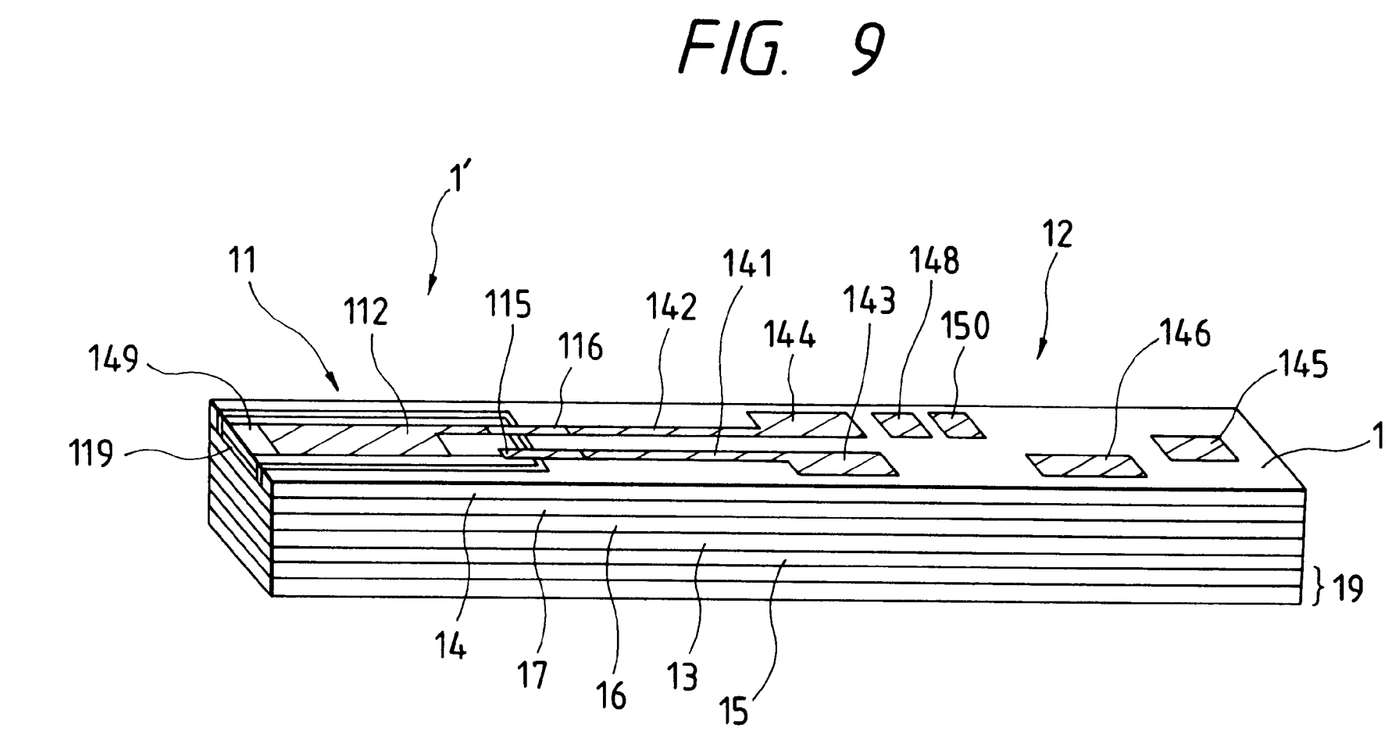
FIG. 9 is a perspective view showing an arrangement of a NOx sensor in accordance with a fourth embodiment of the present invention.
Figure 10:
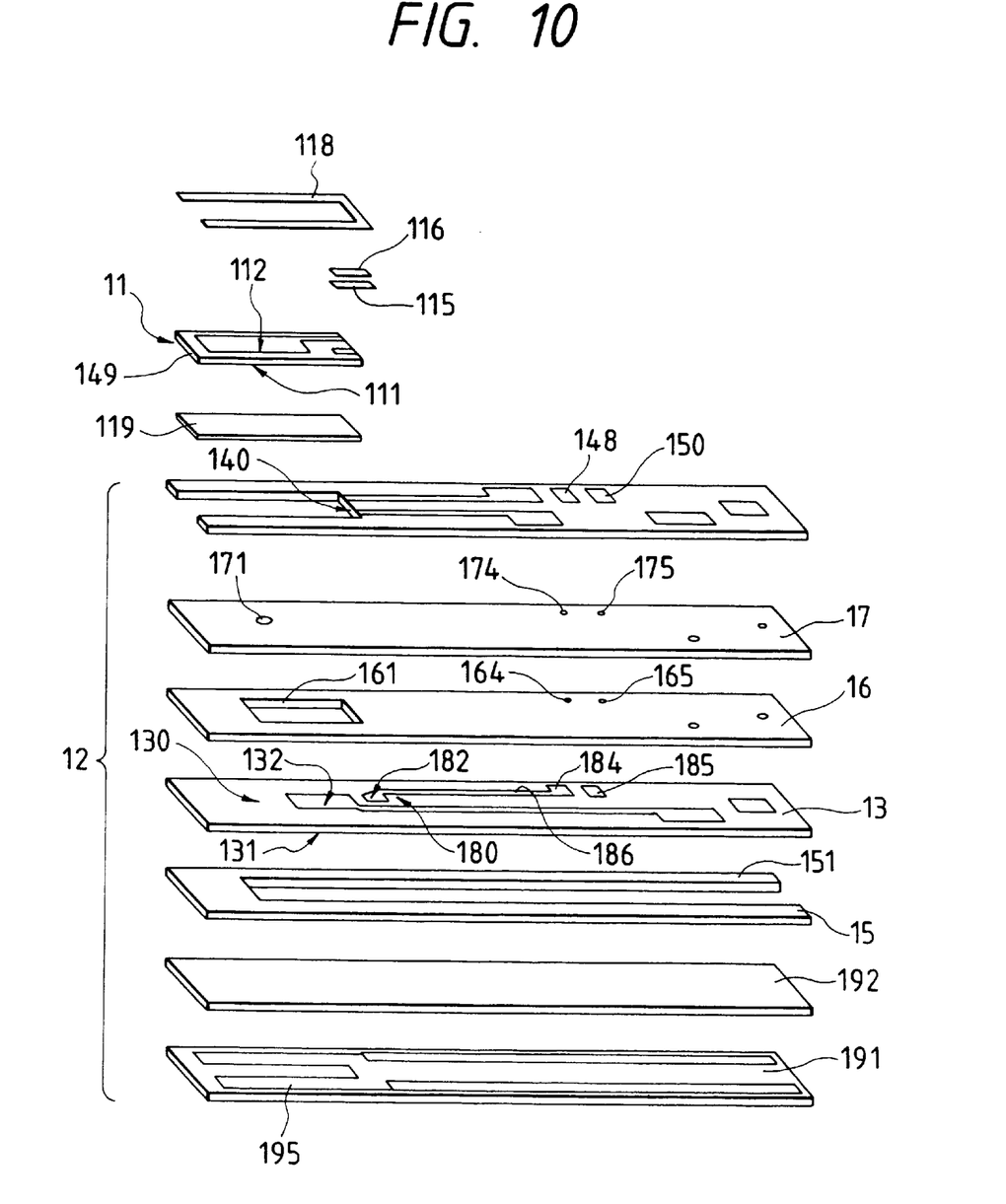
FIG. 10 is an exploded perspective view showing the NOx sensor in accordance with the fourth embodiment of the present invention.

FIGS. 9 and 10 show a NOx sensor 1' in accordance with a fourth embodiment of the present invention. The NOx sensor 1' of the fourth embodiment differs from the first embodiment in that an oxygen sensor cell 180 is provided on the solid electrolytic substrate 13.

The oxygen sensor cell 180 comprises an electrode 182 facing to the sample gas chamber 161 and an electrode (not shown) facing to the reference gas chamber 151. A lead 186 is provided on the upper surface of the solid electrolytic substrate 13 to connect the electrode 182 to an intermediate terminal 184. Similarly, another electrode of the oxygen sensor cell 180 is connected to an intermediate terminal 185 via a lead (not shown) provided on the lower surface of the solid electrolytic substrate 13.

The intermediate terminal 184 is connected to an output terminal 148 via through holes 164 and 174. The other intermediate terminal 185 is connected to an output terminal 150 via through holes 165 and 175. The rest of the fourth embodiment is substantially the same as the first embodiment.

A feedback circuit is provided between the oxygen sensor cell 180 and the pump cell 130 to activate the pump cell 310 based on an output value of the oxygen sensor cell 180. With this arrangement, the oxygen gas concentration in the sample gas chamber 161 can be maintained at a constant value.

Accordingly, the fourth embodiment provides the NOx sensor 1' capable of accurately detecting the NOx concentration of a sample gas.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A sensor for detecting a concentration of NOx in a sample gas, comprising:

a main body having a sensor cell and defining a reference gas chamber and a sample gas chamber therein, said sample gas chamber having a wall formed by a solid electrolytic substrate having an oxygen ion conductivity, and said sensor cell being disposed between said reference gas chamber and said sample gas chamber for detecting a concentration of a NOx gas, and a pump cell body having a surface facing to said sample gas chamber and having a pump cell for introducing and exhausting an oxygen gas to and from said sample gas chamber, wherein no electrode of said sensor cell is contaminated by a substance evaporating from said pump cell during a sintering operation by independently sintering said main body and said pump cell body, wherein said main body has a coupling groove with which said pump cell body is coupled, and said pump cell body is bonded with said main body by an adhesive.

2. A manufacturing method for manufacturing a NOx sensor comprising a main body and a pump cell body, said main body having a sensor cell and defining a reference gas chamber and a sample gas chamber therein, said sample gas chamber having a wall formed by a solid electrolytic substrate having an oxygen ion conductivity, and said sensor cell being disposed between said reference gas chamber and said sample gas chamber for detecting a concentration of a NOx gas, and said pump cell body having a surface facing to said sample gas chamber and having a pump cell for introducing and exhausting an oxygen gas to and from said sample gas chamber, said manufacturing method comprising the steps of:
fabricating said main body and said pump cell body as separate items;
sintering said main body and said pump cell body independently; and
assembling said main body and said pump cell body after finishing the sintering operation to obtain a NOx sensor, this assembling including coupling said pump cell body with a coupling groove formed on said main body and then bonding said pump cell body with said main body by an adhesive.

3. The manufacturing method for manufacturing a NOx sensor in accordance with claim 2, wherein said main body and said pump cell body are sintered independently at a temperature exceeding a melting point of a substance vaporizable from said pump cell.

4. The manufacturing method for manufacturing a NOx sensor in accordance with claim 3, wherein said substance vaporizable from said pump cell is an additive added to suppress an activity of an electrode of said pump cell.

5. The manufacturing method for manufacturing a NOx sensor in accordance with claim 2, wherein this assembling further including thermally processing a united assembly of said main body and said pump cell body at a temperature lower than the melting point of a substance vaporizable from said pumping cell.

* * * * *